United States Patent [19]

Wong

[11] Patent Number: 4,521,210
[45] Date of Patent: Jun. 4, 1985

[54] EYE IMPLANT FOR RELIEVING GLAUCOMA, AND DEVICE AND METHOD FOR USE THEREWITH

[76] Inventor: Vernon G. Wong, 10908 Rosemont Dr., Rockville, Md. 20852

[21] Appl. No.: 453,357

[22] Filed: Dec. 27, 1982

[51] Int. Cl.³ .................. A61M 27/00; A61B 17/00
[52] U.S. Cl. ............................................. 604/8; 3/1; 3/13
[58] Field of Search ....................... 604/8–10, 604/93, 118; 3/1, 13

[56] References Cited

U.S. PATENT DOCUMENTS

| | | | |
|---|---|---|---|
| 3,159,161 | 12/1964 | Ness | 604/8 |
| 3,767,759 | 10/1973 | Wichterle et al. | 264/313 |
| 3,788,327 | 1/1974 | Donowitz et al. | 604/9 |
| 3,915,172 | 10/1975 | Wichterle et al. | 604/8 |
| 4,037,604 | 7/1977 | Newkirk | 604/9 |
| 4,307,723 | 12/1981 | Finney | 604/8 |
| 4,428,746 | 1/1984 | Mendez | 604/8 |

OTHER PUBLICATIONS

"Reduction of Intraocular Pressure using Plastics in Surgery" by R. A. Ellis; American Journal of Ophthalmology, 50, pp. 733–742, 1960.
"Studies on Intraocular Pressure" by Carl Kupfer, Archives of Ophthalmology, 65, pp. 565–570, Apr. 1961.
"Preparation of Surgical Implants from Silicone Rubber by Means of a Postforming Technique" by S. Ore et al., Surgery, Aug. 1962, pp. 385–390, vol. 52, No. 2.

*Primary Examiner*—Ronald L. Frinks
*Attorney, Agent, or Firm*—Albert L. Free

[57] ABSTRACT

An eye implant device for relieving excessive eye pressure due to glaucoma comprises a thin, elongated, resilient, semi-rigid body of biocompatible material such as polymethyl methacrylate, having surface channels extending along its length to provide drainage passages for eye fluids and transverse perforations through it spaced from each other along its length. Preferably the material of the body is wettable by the eye fluids, and the device curved along its length to match the curvature of the interior of the sclera of the eye in the limbal region. The longitudinal channels are preferably provided by corrugating the body of the device longitudinally, and the device is preferably cruciform in shape. It is preferably implanted with its tip in the peripheral angle of the anterior chamber of the eye, with its central portion extending between the sclera and ciliary body to form a cyclodialysis, and through a portion of the sclera, to which it is sutured; the opposite end extends into the suprachoroidal space, wherein eye fluids drained from the anterior chamber are absorbed.

28 Claims, 19 Drawing Figures

EYE IMPLANT FOR RELIEVING GLAUCOMA, AND DEVICE AND METHOD FOR USE THEREWITH

This invention relates to an implant, an implant device and a method of implanting same, for use in the eye to relieve the elevated eye pressure characteristic of glaucoma.

BACKGROUND OF THE INVENTION

Glaucoma is a condition of the eye in which the normal body mechanisms for removing or draining off fluid generated in the eye do not operate effectively, with the result that the internal pressure of the eye rises excessively. With the passage of time, this excessively high internal pressure adversely affects the optic nerve, first causing a severe reduction in peripheral vision and finally complete blindness, unless the condition is successfully treated.

Various liquid medicaments are known which can be dropped periodically onto the eye to limit the elevation of pressure. However, with many patients this procedure is not effective because they do not properly follow the treatment prescribed, due to negligence or to the relatively high cost of the medication. In other cases, the medications available may lose their effectiveness over long periods of treatment.

It has also been known to employ surgical procedures which, in effect, produce leaks in the eyeball through which the excess fluid can escape to the exterior. Surgical attempts have also been made to relieve the pressure by implanting wires, tubes or strips of various materials in the angle between the ciliary body and the sclera, where the absorption of excess fluid normally takes place by natural means, or by drains which extend directly through the frontal portion of the eyeball to the exterior. A procedure known as cyclodialysis is also known, in which a cut is made to separate opposed surfaces of the ciliary body and the adjacent sclera. However, difficulties have been encountered in such surgical procedures, due to overgrowth by tissue, motion of the implanted device over a period of time, clogging of tubes, or infection or other adverse reaction to the implanted material by the eye tissue.

In any event, despite the existence of useful medications and the availability of various surgical and implant techniques, there still remain large numbers of patients who can no longer be helped by such procedures, and who become blind as a result.

Accordingly, it is an object of the invention to provide a new and useful implant, implant device and method of implantation for relieving elevated eye pressure.

Another object is to provide such implant, implant device and implantation procedure which are relatively easy to provide, and which promise to be effective and safe over long periods of time.

Another object is to provide such implant, implant device and implant procedure which will effectively relieve internal eye pressure without objectionable leakage to the exterior of the eye.

SUMMARY OF THE INVENTION

These and other objects of the invention are achieved by the use of a surgical implant comprising a thin body of biocompatible material of a length to extend between the suprachoroidal space of the eye and the normal angle between the sclera and the ciliary body at the periphery of the anterior chamber of the eye, the implant device having at least one open channel along its surface extending between its opposite ends. The device preferably also has perforations extending transversely through it and spaced along its length, and is preferably wettable by the fluids of the anterior chamber of the eye so the fluids may readily flow along the channels and through the perforation.

The device, when implanted, serves to hold apart a portion of the ciliary body and the adjacent sclera thus permitting fluid absorption by the thus-exposed surface of the ciliary body, while at the same time providing passages along and through the device for longitudinal and transverse flow of the liquids normally present in this region. The extension of the longitudinal channels between the angle of the eye and the suprachoroidal space provides a drain path for excess liquid in the eye, permitting fluids to drain off to the suprachoroidal space where they can be absorbed, thus relieving the excess pressure in the eye which could otherwise occur.

In its preferred form, the device of the invention is made of a resilient, preferably non-porous, biocompatible material, curved to follow the configuration of the limbal region of the eye. To facilitate insertion, it preferably has a sharp leading edge, and to assure fixation it is preferably of crucifix form, having a main stem portion extending along its length direction and a cross-arm transverse thereto adapted to be sutured to the sclera at a position between the angle at the periphery of the anterior chamber of the eye and the suprachoroidal space.

According to the preferred procedure of the invention, such a device is preferably implanted as follows. A flap is cut in the conjunctiva extending posteriorly from the limbus, and folded forward to expose the underlying sclera; a flap is then cut part-way through the underlying sclera and folded forward toward the limbus, to expose an underlying bed of sclera. A pair of spaced-apart linear incisions are made through the scleral bed, and the forward end of the implant is urged through the anterior incision nearer the limbus until it extends between the ciliary body and the sclera and into the outer edge of the anterior chamber of the eye, and until the opposite or rearward end of the implant device is forward of the posterior scleral incision. At this point the device is slid backwardly, and the above-mentioned rearward end of the device is tucked through the posterior linear incision into the suprachoroidal space; the cross-arm of the device is preferably longer than the latter incision so as to act as a stop or abutment bearing against the tissue adjacent to the posterior scleral incision. The device is then sutured to the underlying sclera, the scleral flap reclosed by suitable sutures, and the overlying conjunctival flap also resutured to close.

The result is an implant, provided by relatively simple surgical procedures, which will stay in place over very long periods of time, which provides a cyclodialysis to hold the ciliary body and adjacent sclera apart, and which permits lateral and longitudinal fluid flow, including flow to the suprachoroidal space, without likelihood of infection, rejection or migration and without producing objectionable leakage of eye fluid to the exterior of the eye. While there is not universal agreement in the art as to what the most important factors are in the causation of glaucoma, the above-described implant device, implant and procedure are designed to mitigate all of them.

BRIEF DESCRIPTION OF FIGURES

These and other objects and features of the invention will become more readily apparent from a consideration of the following detailed description, taken together with the accompanying drawings, in which.

DETAILED DESCRIPTION OF PREFERRED EMBODIMENTS

Figure 1:
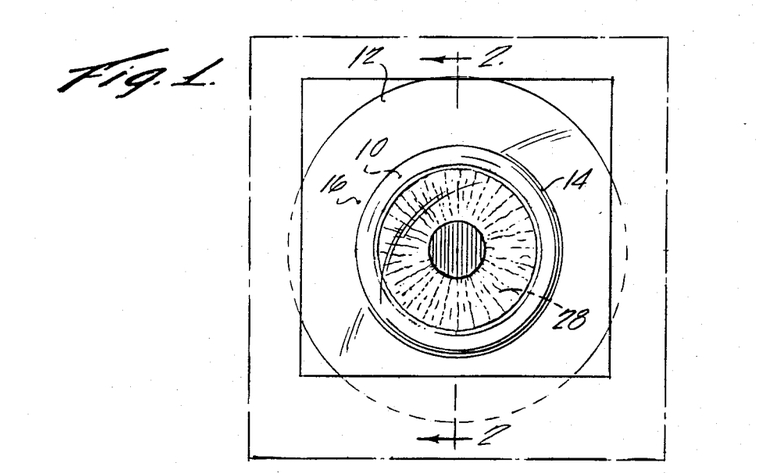
FIG. 1 is a diagrammatic front elevational view of a normal eye, showing the major relevant parts and omitting irrelevant details.
Figure 2:
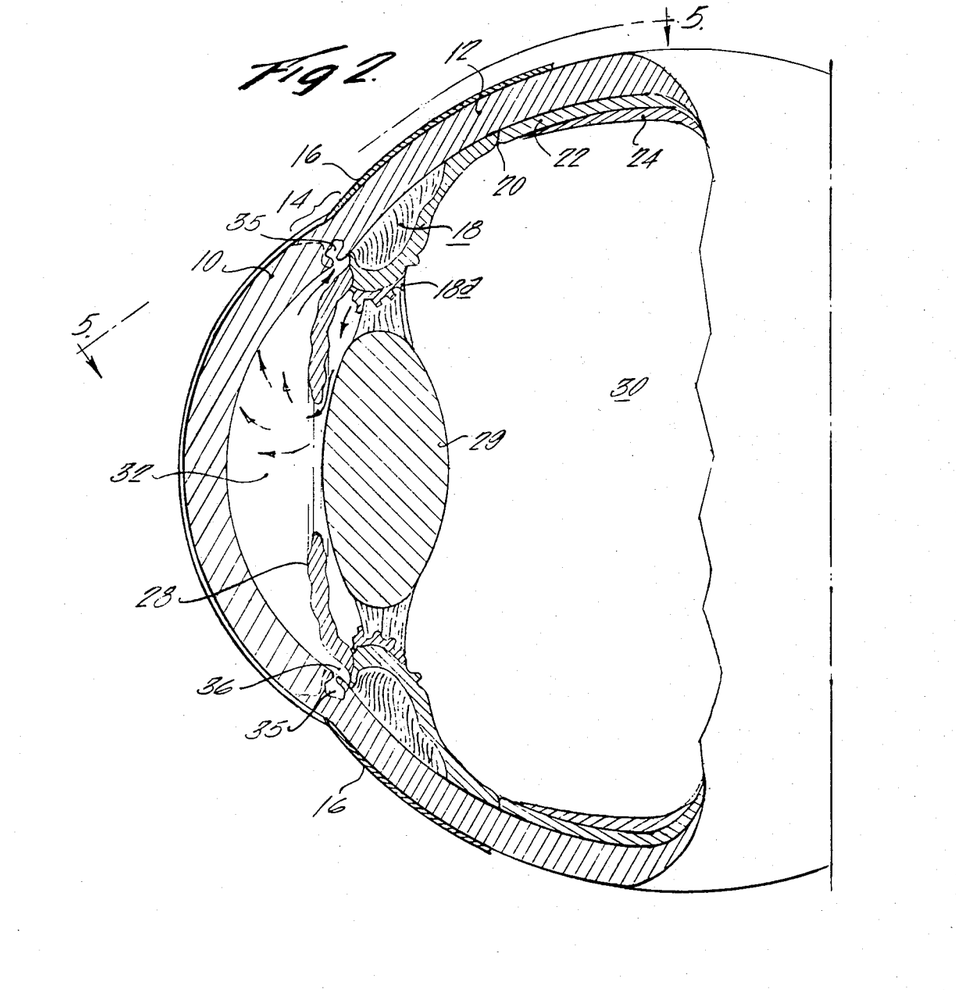
FIG. 2 is an enlarged fragmentary sectional view, taken along lines 2—2 of FIG. 1.

Referring now to the specific embodiment of the invention shown in the drawings by way of example only and illustrating my presently preferred embodiment of the invention, FIGS. 1 and 2 show schematically the relevant parts of a human eye as an aid in understanding the anatomical terminology employed; it will be understood that many irrelevant anatomical details are omitted in the interest of clarity.

As shown, the transparent cornea 10 at the front of the eye merges into the generally spheroidal sclera 12 at an annular junction designated as the limbus 14. The conjunctiva 16 extends posteriorly from the limbus over the front half of the eye and then projects in a forward direction, underlying the upper and lower eyelids. In apposition with the interior side of the sclera, and beginning at the limbus, the ciliary body 18 extends posteriorly until at 20 it becomes the choroid 22, a layer containing many blood vessels. The choroid 22 extends further rearwardly around the back of the interior of the eye, and in turn is covered on its interior surface with the retina 24.

Near the forward end of the ciliary body 18, the diaphragm-like iris 28 extends radially inwardly of the eye to provide automatic control of the amount of light reaching the lens 29, which is positioned just behind the iris. The central portion of the eye rearward of the iris is designated as the vitreous cavity 30, while the portion forward of the iris is designated as the anterior chamber 32, which contains the so-called aqueous humor, a rather thin watery eye fluid.

Research in ophthalmology indicates that the aqueous humor is generated primarily by the ciliary body 18, including the ciliary processes such as 18a, rearward of the iris, and reaches the anterior chamber 32 through the pupil, as indicated by the arrows in FIG. 2, Excess of the aqueous humor is believed to be removed through structures such as 35 located in the Canal of Schlemm, adjacent the peripheral angle 36 of the anterior chamber. Purportedly, it is the failure of this drainage function which, in the glaucomic eye, causes the internal pressure of the eye to rise excessively as new fluid is generated and delivered to the interior eye at a rate faster than it is removed by normal processes.

Figure 3A:
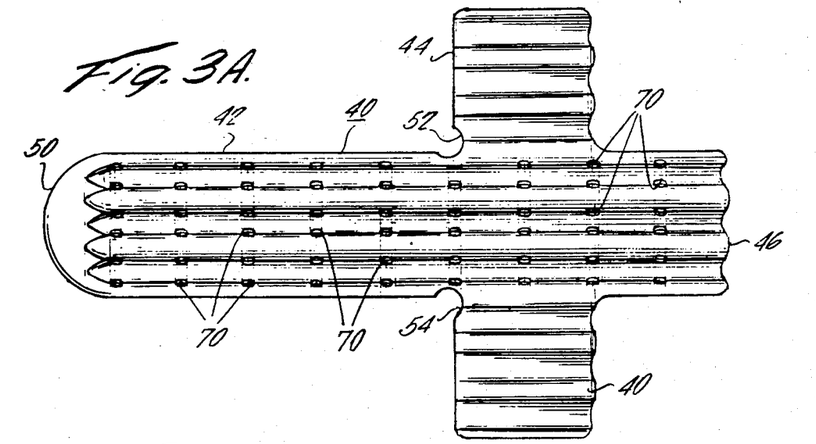
FIG. 3A is a greatly enlarged plan view of an implant device according to a preferred embodiment of the invention.
Figure 3B:
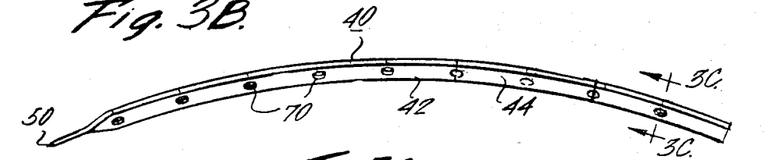
FIG. 3B is a side elevational view of the implant device shown in FIG. 3A.
Figure 3C:
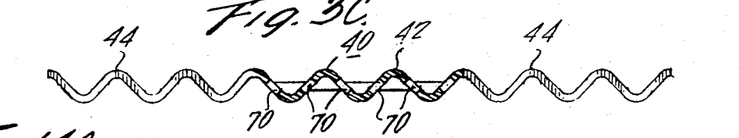
FIG. 3C is an enlarged transverse sectional view taken on the line 3C,3C of FIG. 3B.

Referring now to FIGS. 3A, 3B and 3C which show a preferred form of the implant device of the invention, there is shown an elongated thin body 40 of biocompatible material which is wettable by the aqueous humor, and may for example comprise polymethyl methacrylate, preferably in a form which is semi-rigid yet resilient. In this example the implant device is cruciform, having a main stem portion 42 and an integral transverse cross-arm 44 near, but spaced from, one end 46 thereof. The implant device 40 is preferably curved along its length with a radius of curvature similar to the curvature of the interior side of the sclera adjacent to the ciliary body, against which it will lie when implanted. In a preferred embodiment, the width of the stem 42 may be about 2 mm and its overall length about 10 mm; the overall width of the cross-arm portion may be about 6 mm, so as to extend about 2 mm on each side of the stem portion 42; the cross-arm 44 may be about 2 mm from the adjacent end 46 of the stem portion, and have a dimension along the direction of the stem of about 2 mm.

All corners of the device are preferably rounded off, except that the front end portion 50 is preferably beveled to provide a sharp edge for purposes described hereinafter. Notches 52 and 54 are preferably provided adjacent the junction of the cross-arm 44 with the longer part of the stem 42, in which notched sutures may be placed to stabilize the implant device in final position as described hereinafter.

In accordance with the invention, the implant device is provided with surface channels extending along its length to permit the flow of eye fluid from one end to the other thereof. In the present example, these channels are provided by making the implant of a single corrugated piece, these corrugations being shown especially clearly in the end view of FIG. 3C. It is also deemed preferable to provide the perforations such as 70 extending transversely through the implant device, in this example extending through the side walls of the corrugations, so as not to be closed by opposed tissue when the implant device is in place. In this example there are three corrugations in the stem portion, and three more corrugations in each of the two protruding "wings" of the cross-arm. In a typical example, the thickness of the implant device is about 0.3 mm, the radius of curvature of the implant device along its length is about 1.2 cm and the depth of the corrugations is about 1 mm.

Figure 4:
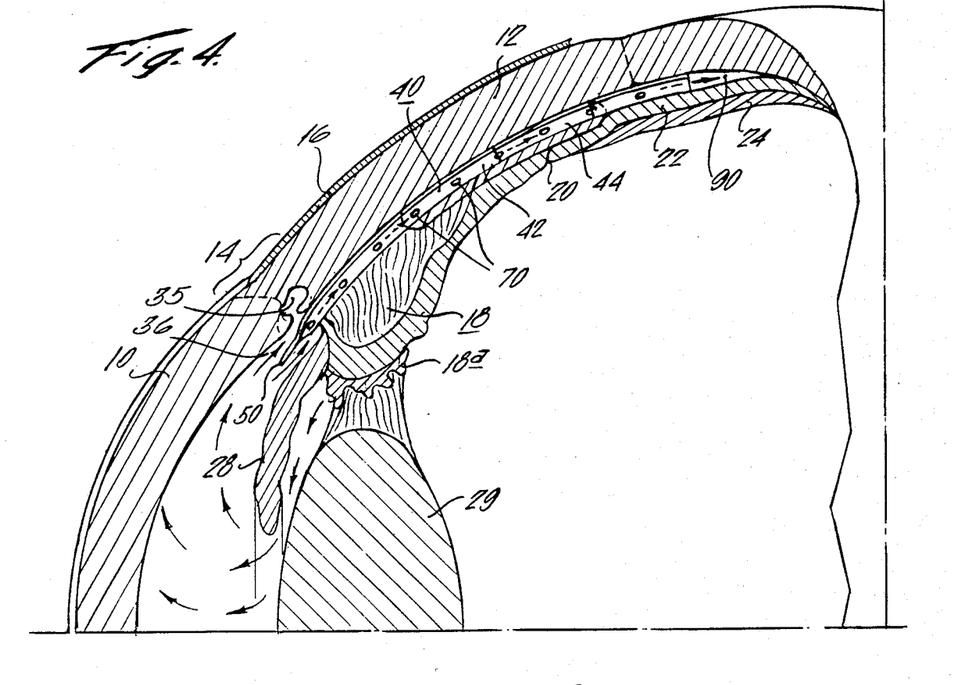
FIG. 4 is a greatly enlarged fragmentary sectional view similar to FIG. 2 but showing at a greater scale the eye and implant device after implantation of the device in the eye.
Figure 5:
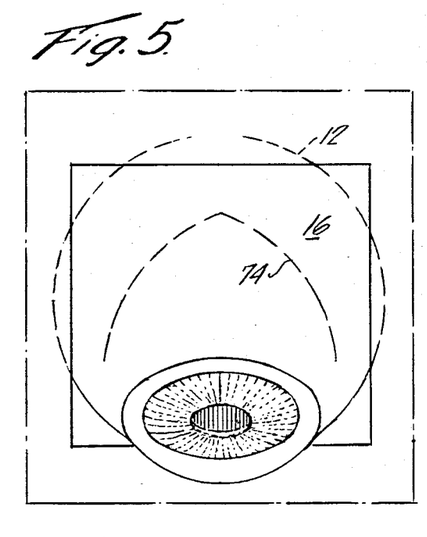
FIGS. 5-13 are diagrammatic views of a portion of the eye, to convenient scales, showing successive steps in the preferred procedure for implanting the device of FIGS. 3A, 3B and 3C in the eye.

FIG. 4 shows the implant device 40 in place, separating the sclera 12 from a portion of the ciliary body 18, and providing longitudinal surface channels for fluid flow from the peripheral angle 36 of the eye to the suprachoroidal space 90.

Figure 6:
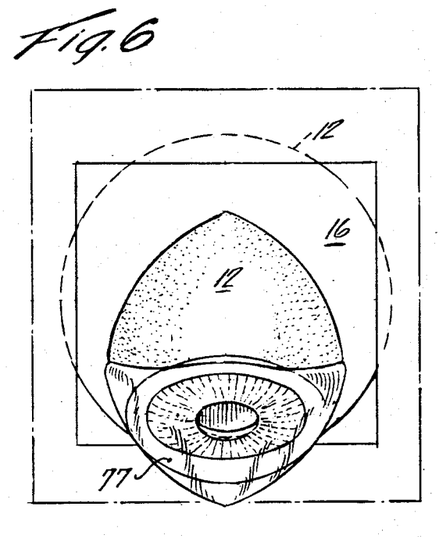

Turning now to FIGS. 5-13 showing the preferred surgical procedure for implanting the prosthetic implant device, the large squares shown in solid line in these figures indicate the field of surgical operation. After normal preoperative preparation of the operation site, an incision is made through the conjunctiva along the broken line 74 shown in FIG. 5. As shown in FIG. 6, the resultant conjunctival flap 77 is retracted forwardly to expose the underlying sclera 12.

Figure 7:
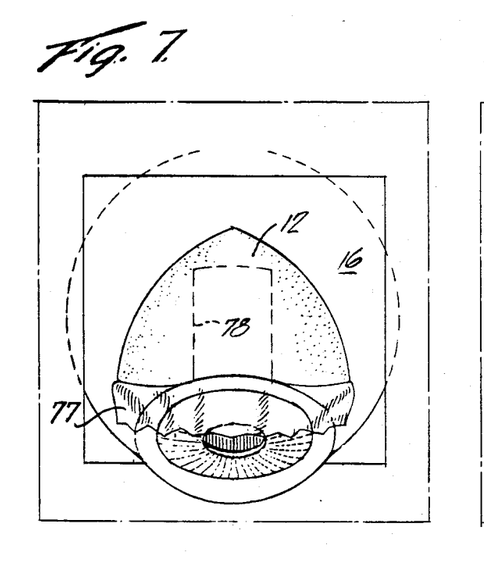
Figure 8:
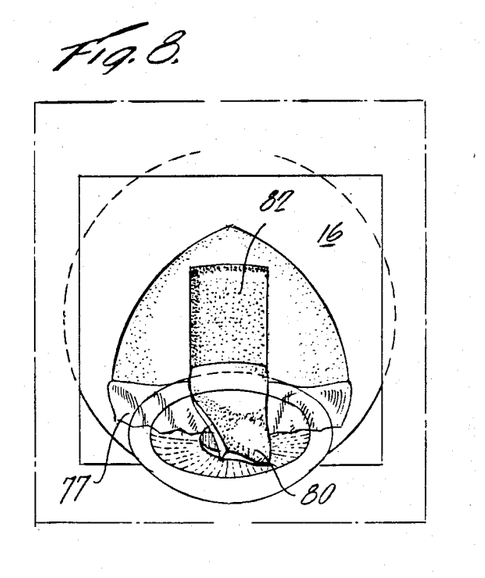

As shown in FIG. 7, a partial incision is then made along the broken lines 78, which incision extends only part-way through the underlying sclera to form a scleral flap 80 (FIG. 8). As shown in FIG. 8, this scleral flap is retracted to expose an underlying scleral bed 82.

Figure 9:
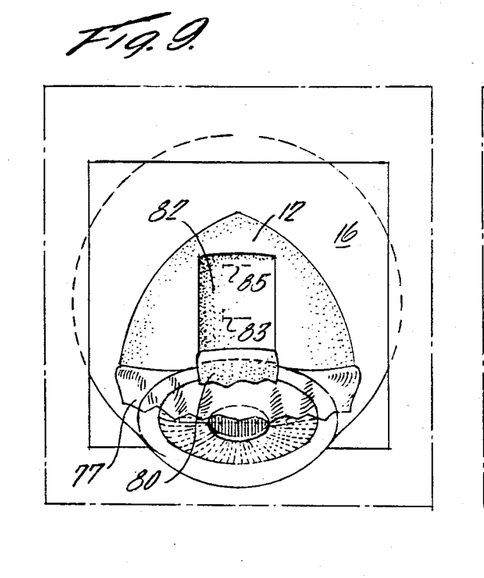
Figure 10:
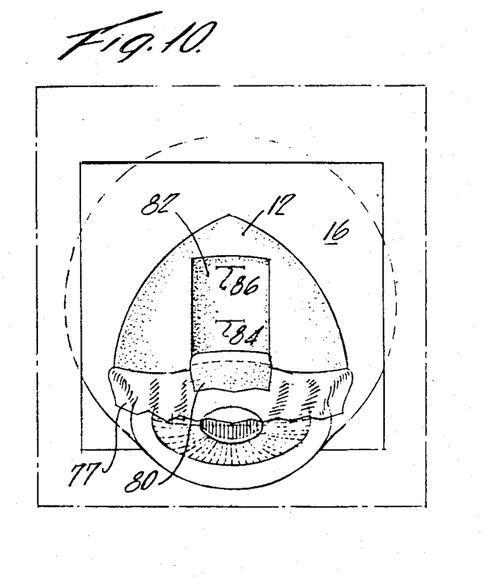

Next, as illustrated in FIGS. 9 and 10, two incisions or sclerotomies 84 and 86 are formed parallel to each other in the scleral bed at the positions marked by broken lines 83 and 85, each of which may be about 2 mm in length. The anterior incision 84 extends generally parallel to a tangent to the limbus, and preferably about 4 mm posterior to the limbus; the posterior incision 86 is preferably parallel to the anterior incision and adjacent the posterior terminus of the scleral bed. Typically, the scleral bed may be about 6 mm wide and 8 mm in length, so that the posterior incision typically is of the order of 1 mm from the beginning of the underlying choroid. Both incisions extend inwardly just to the underlying ciliary body 18.

Figure 11:
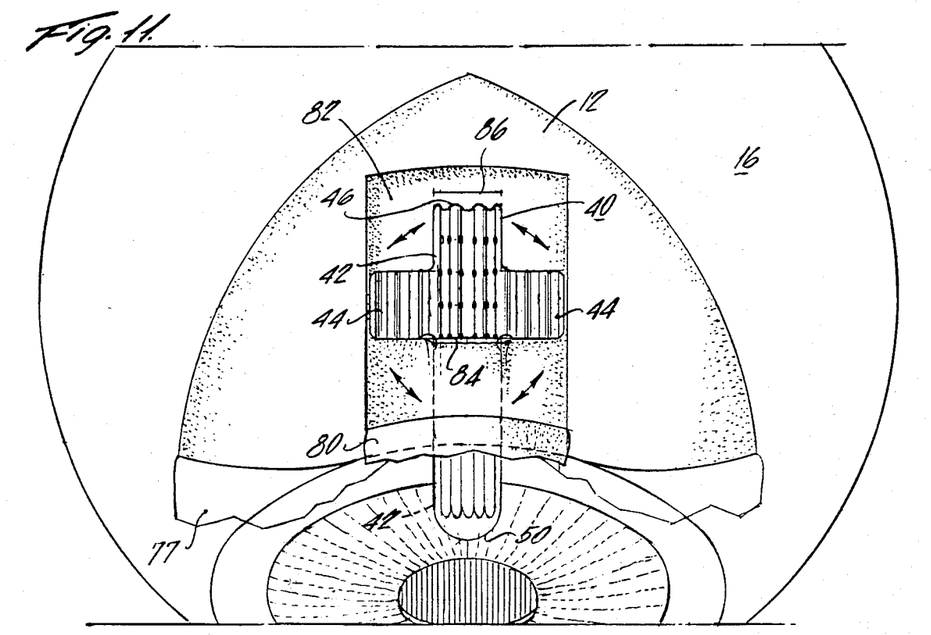
Figure 12:
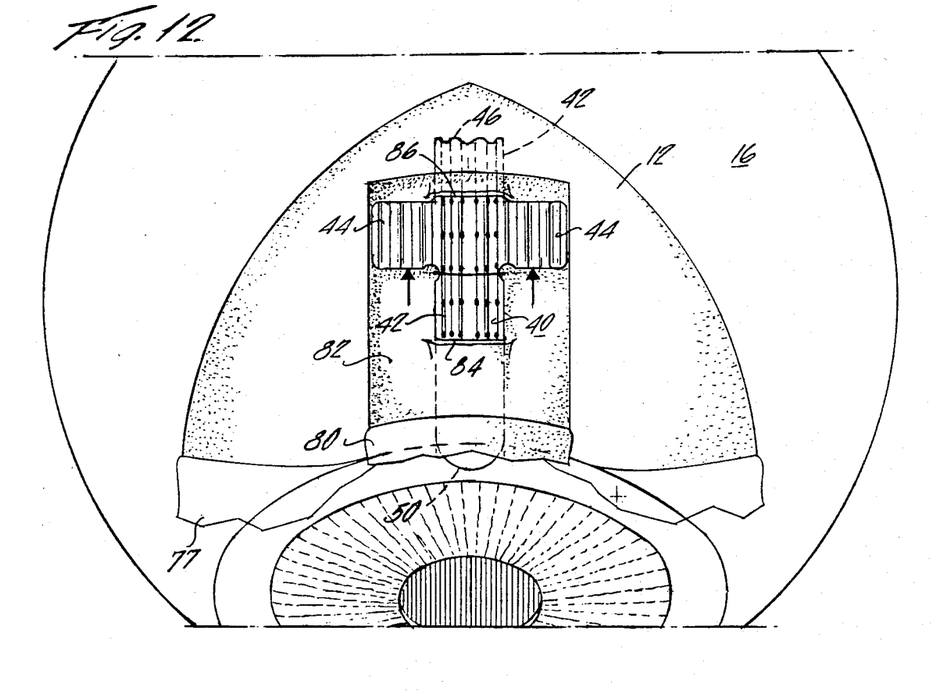

A cyclodialysis is then accomplished through the anterior incision 84, to separate the underlying ciliary body 18 from the anterior side of the overlying sclera 12. While this can be done with a special separate surgical instrument, I presently prefer to utilize the implant device itself for this purpose. Accordingly, as illustrated in FIG. 11, the sharpened front end 50 of the implant device is inserted into the anterior incision 84 and worked back-and-forth and forwardly along the boundary between the underlying ciliary body 18 and the inner side of the adjacent sclera 12 until it reaches a position such as that shown in FIG. 11. In this position, the leading end 50 of the implant device 40 extends into the peripheral angle 36 of the anterior chamber 32 of the eye, and further forward motion is arrested by the cross-arm 44, which cannot traverse the smaller anterior incision 84; at this point, the implant device is slid rearwardly, and the posterior end 46 of the implant device 40 is tucked into and through the posterior incision 86, with the posterior end of the implant then entering the suprachoroidal space 90 (FIG. 4) between the sclera and the choroid, to achieve the final position for the implant device illustrated in FIG. 4.

The implant device, being now held against further rearward motion through incision 86 by the cross-arm 44, is held against forward motion and other migrational motion by suturing it to the underlying sclera. For this purpose, it is convenient to pass the sutures across the stem of the implant device and through the opposed notches 52 and 54, to provide a positive securing effect, although other securing techniques may be used if desired.

Figure 13:
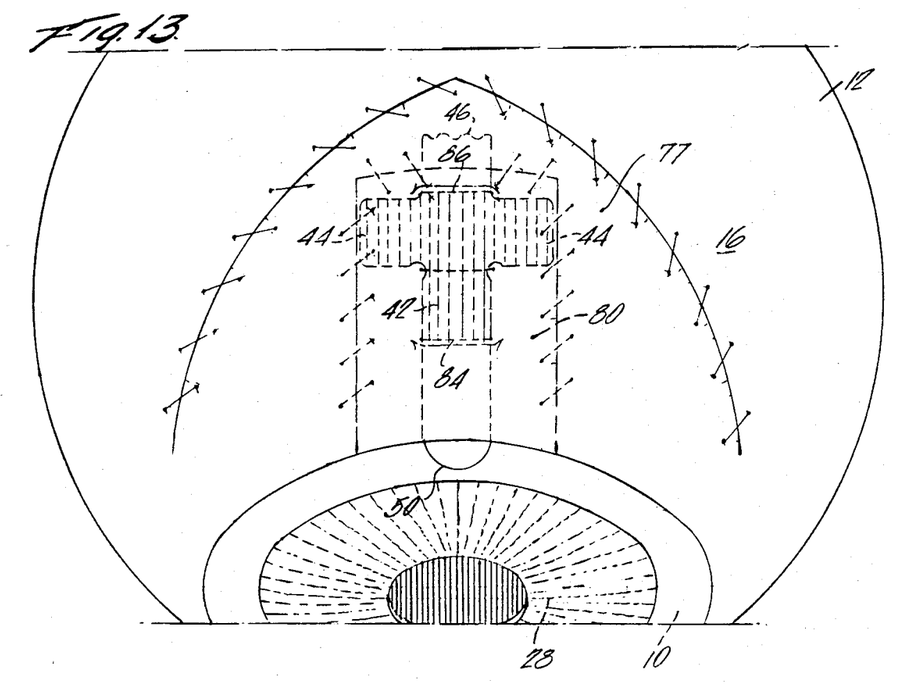

As illustrated by FIG. 13, the scleral flap 80 is then repositioned and sutured to the adjacent sclera, and the conjunctival flap then repositioned and sutured to the adjacent conjunctiva, and on top of the scleral flap.

Referring especially to FIGS. 4 and 13 then, it will be seen that upon implantation the implant device 40 forms a cyclodialysis and holds a part of the ciliary body away from the interior side of the adjacent sclera, with the sclera and ciliary body resting on the tops of the opposed corrugations, with the forward end 50 of the device 40 extending into the peripheral angle 36 in the anterior chamber of the eye, with the corrugations of the implant device providing longitudinal channels extending from the latter angle to the suprachoroidal space 90, and with the transverse perforations 70 providing transverse communication for fluid through the implant device along its length. Fluid thus delivered to the suprachoroidal space will be absorbed therein, and additional reduction of fluid pressure is to be expected due to the cyclodialysis. The curvature of the implant device facilitates its proper insertion and location along the correspondingly curved interior surface of the sclera, and the cross-arm 44 not only aids in the fixation of the longitudinal position of the implant device but also aids in holding the scleral flap away from the scleral bed after the operation is completed, thus reducing the possibility of harmful adhesions which would impede the fluid flow. Accordingly, an implant suitable for reducing fluid pressure in the eye has been provided, which is readily installed, highly effective and capable of long operative life without infection or rejection.

While the embodiment of the implant device shown in the foregoing figures utilizing corrugations along its length is presently preferred, it is contemplated that other arrangements could be employed to provide the desired fluid communication along the length of the device by means of surface channels.

Figure 14A:
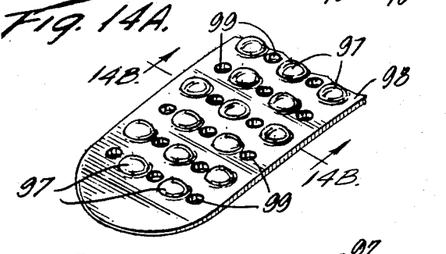
FIG. 14A is a fragmentary pictorial view of a portion of a modified implant device similar to FIG. 3A but showing a pattern of bumps or mounds rather than corrugations.
Figure 14B:
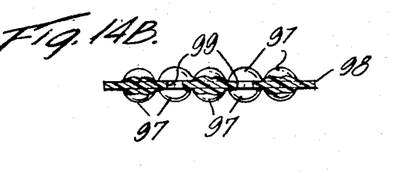
FIG. 14B is a sectional view taken on the line 14B,14B of FIG. 14A, showing details of bumps and holes.

For example, FIGS. 14A and 14B illustrate one possible form of implant device in which surface channels for fluid flow are provided by forming a plurality of mounds or bumps 97 along both surfaces of the device 98 against which the opposing tissues will rest after implantation, while still leaving channels for liquid flow along the device between the mounds or bumps. Cross flow is provided by communicating holes 99. Other possible configurations for achieving these same functions will occur to one skilled in the art.

Figure 15A:
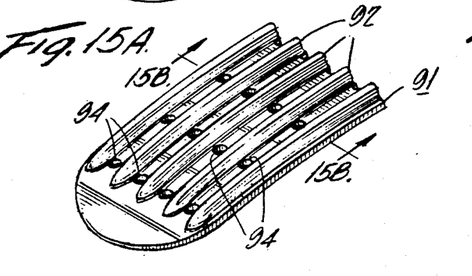
FIG. 15A is a view similar to FIG. 14A but illustrating an additional modification using ridges rather than smoothly-curving corrugations.
Figure 15B:
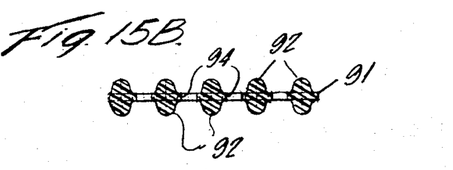
FIG. 15B is a sectional view taken on the line 15B,15B of FIG. 15A showing details of ridges and holes.

FIGS. 15A and 15B show another such arrangement utilizing an implant device made up of a strip of biocompatible material 91 having parallel longitudinally extending ridges or bars such as 92, forming longitudinal channels between them. Also shown are small communicating holes 94 located between the ridges and radially spaced along the central web.

Some other materials contemplated for the composition of the body of the implant device, or for at least coating its surface, include Pyrolite or Biolete, materials available from CarboMedics, Inc., of Freeport, Tex.

The bumps and ridges shown in FIGS. 14A,B and 15A,B may if desired be placed on only one surface of the body, the opposite side being smooth. Also, in some cases a single surface flow path may be provided, as by using a single corrugation or trough as an implant, although this is deemed less desirable than the other versions shown.

Where deemed appropriate to produce a greater degree of pressure relief, additional or identical or similar implant devices may be implanted as described at various other angular positions about the axis of the same eye. It is contemplated that at least five such implants may be used in the same eye.

Although it is presently preferred that the implant extend to the choroid, it is believed that at least some of the advantages of the invention may be realized by use of an implant which extends from the limbal angle only part-way to the choroid, terminating for example between the sclera and the ciliary body.

Thus while the invention has been described with particular reference to specific embodiments thereof in the interest of complete definiteness, it will be understood that it may be embodied in forms diverse from those specifically shown and described, without departing from the spirit and scope of the invention as defined by the appended claims.

What is claimed is:

1. A surgical implant device adapted for use in the eye to relieve excess eye pressure by drainage of eye fluids from the limbal angle of the anterior chamber of the eye, comprising:

a thin body of biocompatible material of a length and shape adapted to extend along the interior of the sclera from the limbal angle of the anterior chamber of the eye to the choroid of the eye;

said body having at least one outwardly-opening surface channel extending along its length for a distance great enough to extend from said limbal angle to said choroid.

2. The device of claim 1, wherein each of said at least one channel is formed by longitudinal corrugations in said body.

3. The device of claim 1, wherein said body has perforations extending through its thickness dimension.

4. The device of claim 3, wherein said perforations are spaced apart from each other along the length of said body.

5. The device of claim 2, wherein said body comprises perforations extending through the side walls of said corrugations.

6. The device of claim 1, wherein said material of said body is wettable by eye fluids.

7. The device of claim 1, wherein said material is polymethyl methacrylate.

8. The device of claim 1, wherein said body is curved along its length to conform with the curvature of the interior of the sclera in the limbal region of the eye.

9. The device of claim 1, wherein one end of said body has a sharp forward edge.

10. The device of claim 1, wherein said body has a smooth curved configuration at one end thereof, extending across its width dimension.

11. The device of claim 1, wherein said body is resilient but semi-rigid.

12. The device of claim 1, wherein the surface of said body is non-porous.

13. The device of claim 1, wherein said body has a stem portion and an integral cross-arm extending transversely of said stem portion, adjacent but spaced from one end of said stem portion.

14. The device of claim 13, wherein said body has at least a pair of notches in its opposed edges to facilitate suturing of said body to the eye tissue.

15. A surgical implant device for use in an eye subject to glaucoma, comprising:

a thin body of semi-rigid, resilient, biocompatible material which is wettable by liquids of the eye, said body being of the order of 10 mm in length, of the order of 6 mm in width and of the order of 0.3 mm in thickness and in the configuration of a crucifix having a main stem and a cross-arm;

the top of said main stem remote from the cross-arm of said crucifix having a sharp edge;

said body having a radius of curvature along its length of about 1.2 cm;

said body being corrugated along its length dimension to provide channels extending from one end to the other thereof;

said body having perforations extending transversely through the sides of said corrugations, about 1 mm apart and of a diameter of about (5–0 suture).

16. The device of claim 15, wherein said body is of polymethyl methacrylate.

17. The device of claim 16, wherein said main stem has a reduced width adjacent said cross-arm for fixation by sutures.

18. A surgical eye implant for relieving excess eye pressure comprising:

a thin prosthetic device of biocompatible material, one end portion of which is adapted to extend between the ciliary body and the sclera of the eye and into the peripheral angle of the anterior chamber of the eye, the remainder of said device having a shape and extent to extend along and through the sclera to the suprachoroidal space of the eye;

said device having at least one channel at the surface thereof with a length of such extent for extending from said peripheral angle to said suprachoroidal space.

19. The implant of claim 18, wherein said at least one channel comprises corrugations in said device extending along the length thereof.

20. The implant of claim 18, wherein said device has perforations extending transversely through its thickness and positioned along the length thereof.

21. The implant of claim 18, wherein said material is wettable by eye fluids.

22. The implant of claim 18, wherein said material is polymethyl methacrylate.

23. The implant of claim 18, wherein said remainder of said device comprises an integral cross-arm adapted to be positioned in said sclera.

24. The implant of claim 18, comprising sutures for securing a portion of said remainder of said device to, and interior of, said sclera.

25. The method of providing an eye implant for relieving excess eye pressure, comprising:

cutting a flap in and through the conjunctiva to expose the underlying sclera from a position adjacent to the limbus to a position above the underlying choroid;

cutting part-way through said exposed sclera to form a scleral flap and to define an underlying scleral bed extending from a position adjacent the limbus to a position adjacent the choroid;

making an anterior incision through said scleral bed adjacent to the limbus to form a sclerotomy;

making a posterior incision through said scleral bed on the side of said anterior incision toward the choroid to form another sclerotomy;

providing a thin prosthetic implant device of biocompatible material having at least one surface channel extending along its length;

inserting one end of said device through said first incision, and along a path between the ciliary body and the sclera, into the peripheral angle of the anterior chamber of the eye, until the opposite end of said device lies between said anterior and posterior incisions;

thereafter sliding said device lengthwise in the posterior direction, inserting said opposite end of said device through said posterior incision, and continuing said sliding motion until said opposite end enters the suprachoroidal space;

thereafter, suturing said device to the scleral bed while said one end of said device is in said peripheral angle and said opposite end is in said suprachoroidal space, and successively closing said scleral flap and said conjunctival flap.

26. The method of claim 25, wherein said device is formed in the shape of a crucifix with a stem portion and a cross-arm portion, said cross-arm being of greater length than said posterior incision and positioned on said scleral bed against said incision at the time of said suturing of said device to said sclera.

27. The method of claim 25, wherein said one end of said device is tapered to a sharp edge, and is advanced between said sclera and said ciliary body without previously separating said sclera from said ciliary body.

28. A surgical implant device for use in the eye to relieve excess eye pressure, comprising:

a thin body of biocompatible material having at least one externally-open surface channel of a length to extend from the limbal angle of the anterior chamber of the eye toward the choroid of the eye, at least as far as the ciliary body.

* * * * *